US006488780B2

(12) United States Patent
Cauwet-Martin

(10) Patent No.: US 6,488,780 B2
(45) Date of Patent: *Dec. 3, 2002

(54) DETERGENT COSMETIC COMPOSITIONS AND USE THEREOF

(75) Inventor: Daniéle Cauwet-Martin, Paris (FR)

(73) Assignee: L'Oreal S.A., Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 11 days.

This patent is subject to a terminal disclaimer.

(21) Appl. No.: 09/308,267

(22) PCT Filed: Oct. 10, 1997

(86) PCT No.: PCT/FR97/01815

§ 371 (c)(1),
(2), (4) Date: May 17, 1999

(87) PCT Pub. No.: WO98/22087

PCT Pub. Date: May 28, 1998

(65) Prior Publication Data

US 2002/0032134 A1 Mar. 14, 2002

(30) Foreign Application Priority Data

Nov. 15, 1996 (FR) ............................................ 96/13977
Mar. 18, 1997 (FR) ............................................ 97/03280

(51) Int. Cl.$^7$ .......................... A61K 7/075; C11D 1/00; C11D 1/88

(52) U.S. Cl. .......................... 134/42; 510/122; 510/125; 510/127; 510/129; 510/136; 510/159; 510/405; 510/466; 510/481; 510/504; 424/70.12; 424/70.19; 424/70.21; 424/70.24; 424/70.28; 424/450; 514/938; 252/304; 252/312

(58) Field of Search ................................ 510/122, 125, 510/127, 129, 136, 154, 405, 466, 481, 504; 424/70.12, 70.19, 70.21, 70.24, 70.28, 450; 514/938; 134/42; 252/304, 312

(56) References Cited

U.S. PATENT DOCUMENTS

| 2,528,378 | A | | 10/1950 | Mannheimer | 260/309.6 |
|---|---|---|---|---|---|
| 2,781,354 | A | | 2/1957 | Mannheimer | 260/309.6 |
| 4,137,180 | A | | 1/1979 | Naik et al. | 252/8.8 |
| 4,874,554 | A | | 10/1989 | Lange et al. | 260/404 |
| 5,364,633 | A | | 11/1994 | Hill et al. | 424/450 |
| 5,411,744 | A | | 5/1995 | Hill et al. | 424/450 |
| 5,665,687 | A | | 9/1997 | Khayat et al. | 510/136 |
| 5,753,241 | A | * | 5/1998 | Ribier et al. | 424/401 |
| 5,925,341 | A | * | 7/1999 | Cervantes et al. | 424/78.03 |
| 5,958,433 | A | * | 9/1999 | Simonnet | 424/401 |

FOREIGN PATENT DOCUMENTS

| EP | 0 007 120 | 1/1980 |
|---|---|---|
| EP | 0 337 354 | 10/1989 |
| EP | 0 355 368 | 2/1990 |
| EP | 0 692 236 | 1/1996 |
| FR | 2 270 846 | 12/1975 |
| FR | 2 470 596 | 6/1981 |
| FR | 2 519 863 | 7/1983 |
| FR | 2 598 611 | 11/1987 |

OTHER PUBLICATIONS

"Oils in Water", Manufacturing Chemist, vol. 60, No. 1, Jan. 1989, Woolwich, London, pp. 38–40.
M.R. Porter, Handbook of Surfactants, Blackie & Son (Glasgow and London), 1991, pp. 116–178. No Month Given.
English language Derwent Abstract of FR 2 270 846. Dec. 12, 1975.
English language Derwent Abstract of FR 2 470 596, Jun. 12, 1981.
English language Derwent Abstract of FR 2 519 863. Jul. 22, 1983.
English language Derwent Abstract of FR 2 598 611. Nov. 20, 1987.

* cited by examiner

*Primary Examiner*—Yogendra N. Gupta
*Assistant Examiner*—Brian P. Mruk
(74) *Attorney, Agent, or Firm*—Finnegan, Henderson, Farabow, Garrett and Dunner, L.L.P.

(57) ABSTRACT

Detergent and conditioning compositions having a washing base and a conditioning system with an oil nanoemulsion.

47 Claims, No Drawings

DETERGENT COSMETIC COMPOSITIONS AND USE THEREOF

The present invention relates to new cosmetic compositions with improved properties intended simultaneously for cleaning and for conditioning keratinous substances, such as hair, and comprising, in a cosmetically acceptable aqueous vehicle, a washing base composed of surface-active agents with a detergent power in which is also present, as conditioning agent, a nanoemulsion defined below. The invention also relates to the use of the said compositions in the abovementioned cosmetic application.

Detergent compositions (such as shampoos) based essentially on conventional surface-active agents of, in particular, anionic, non-ionic and/or amphoteric type, but more particularly of anionic type, are commonly used for cleaning and/or washing keratinous substances, such as hair. These compositions are applied to wet hair and the foam generated by massaging or rubbing with the hands makes it possible, after rinsing with water, to remove the various types of dirt initially present on the hair.

These base compositions certainly have a good washing power but the intrinsic cosmetic properties which are attached to them remain fairly weak, however, in particular because of the fact that the relatively aggressive nature of such a cleaning treatment can, in the long term, result in more or less marked damage to the hair fibre, in particular with the gradual removal of the lipids or proteins held in or at the surface of the hair fibre.

Consequently, in order to improve the cosmetic properties of the above detergent compositions, and more particularly of those which are called upon to be applied to sensitized hair (i.e. hair which is found to be damaged or embrittled, in particular under the chemical action of atmospheric agents and/or of hair treatments, such as permanent waves, dyings or bleachings), it is now usual to introduce into the latter additional cosmetic agents, known as conditioning agents, intended mainly to repair or limit the harmful or undesirable effects induced by the various treatments or attacks to which the hair fibres are more or less repeatedly subjected. These conditioning agents can, of course, also improve the cosmetic behaviour of natural hair.

It has already been proposed to use vegetable or animal oils for this purpose. On account of the insoluble nature of the oils which can be used in washing and conditioning compositions, the aim is to maintain the oils as an even dispersion in the medium without, however, causing a fall in the viscosity and a decline in the detergent and foaming properties of the compositions. The oils must also be carried to the keratinous substances treated with a view to conferring on them, depending on the application, properties of softness, of gloss and of disentangling, without conferring a greasy nature.

Thus, following considerable research carried out on the question, it has now been found by the Applicant Company that, while using (A) a washing base and (B) a conditioning system comprising at least one oil-in-water emulsion having oil globules with a mean size of less than 150 nm and comprising an amphiphilic lipid phase which comprises at least one non-ionic amphiphilic lipid which is liquid at an ambient temperature of less than 45° C., it is possible to obtain stable detergent compositions exhibiting excellent cosmetic properties, in particular the ease of styling, the form retention, the liveliness and the body of the treated hair, while retaining their good intrinsic washing power and in particular their foaming power.

These new compositions make it possible to deposit a larger amount of oil on hair than with a conventional emulsion but without a greasy feel or visual appearance.

The compositions in accordance with the invention confer on hair, after rinsing, a notable treating effect which is displayed in particular by an ease of disentangling and a contribution of body, lightness, sleekness, softness and suppleness, without any feeling of greasiness.

Thus, the subject of the present invention is new detergent and conditioning compositions, characterized in that they comprise, in a cosmetically acceptable aqueous medium, (A) a washing base and (B) a conditioning system comprising at least one oil-in-water emulsion having oil globules with a mean size of less than 150 nm and comprising an amphiphilic lipid phase, this amphiphilic lipid phase comprising at least one non-ionic amphiphilic lipid which is liquid at an ambient temperature of less than 45° C.

Another subject of the invention is the use in cosmetics of the above compositions for cleaning and/or removing make-up from and/or conditioning keratinous substances, such as hair and skin.

As indicated above, the essential components forming part of the composition of the products according to the invention are (A) a washing base and (B) a conditioning system comprising at least one oil-in-water emulsion having oil globules with a mean size of less than 150 nm and comprising an amphiphilic lipid phase, characterized in that the amphiphilic lipid phase comprises at least one non-ionic amphiphilic lipid which is liquid at an ambient temperature of less than 45° C.

A—WASHING BASE:

The compositions in accordance with the invention necessarily comprise a washing base, generally an aqueous washing base.

The surfactant or surfactants forming the washing base can be chosen without distinction, alone or as mixtures, from anionic, amphoteric, non-ionic and cationic surfactants.

However, according to the invention, the washing base preferably comprises anionic surfactants or mixtures of anionic surfactants and of amphoteric surfactants and, more preferentially still, contains only this type of surfactant or mixture of surfactants.

The minimum amount of washing base is that just sufficient to confer a satisfactory foaming and/or detergent power on the final composition, whereas excessively large amounts of washing base do not really contribute additional advantages.

Thus, according to the invention, the washing base can represent from 4% to 50% by weight, preferably from 10% to 35% by weight and more preferentially still from 12% to 25% by weight of the total weight of the final composition.

The surfactants which are suitable for implementing the present invention are in particular the following:

(i) Anionic surfactant(s):

Their nature does not assume a really critical character within the context of the present invention.

Thus, by way of example of anionic surfactants that can be used, alone or as mixtures, in the context of the present invention, there may be mentioned in particular (nonlimiting list) the salts (in particular alkali metal, especially sodium, salts, ammonium salts, amine salts, aminoalcohol salts or magnesium salts) of the following compounds: alkyl sulphates, alkyl ether sulphates, alkylamido ether sulphates, alkylarylpolyether sulphates, monoglyceride sulphates; alkylsulphonates, alkyl phosphates, alkylamidesulphonates, alkylarylsulphonates, α-olefinsulphonates, paraffinsulphonates; alkyl sulphosuccinates, alkyl ether sulphosuccinates, alkylamidesulphosuccinates; alkyl sulphosuccinamates; alkyl sulphoacetates; alkyl ether phosphates; acylsarcosinates; acylisethionates and N-acyltaurates, the alkyl or acyl radical of all these different compounds preferably containing from 12 to 20 carbon atoms, and the aryl radical preferably denoting a phenyl or benzyl group. Among the anionic surfactants which are further usable, there may also be mentioned the salts of fatty acids such as the salts of oleic, ricinoleic, palmitic and stearic acids, the acids of copra oil or of hydrogenated copra oil, and acyllactylates in which the acyl radical contains 8 to 20 carbon atoms. It is also possible to use weakly anionic surfactants, like alkyl-D-galactosideuronic acids and salts thereof, as well as the polyoxyalkylenated ($C_6$–$C_{24}$)alkyl ether carboxylic acids, the polyoxyalkylenated ($C_6$–$C_{24}$)alkylaryl ether carboxylic acids, the polyoxyalkylenated ($C_6$–$C_{24}$)alkylamido ether carboxylic acids and salts thereof, in particular those containing from 2 to 50 ethylene oxide groups, and mixtures thereof.

Among the anionic surfactants, it is preferable to use, according to the invention, alkyl sulphate and alkyl ether sulphate salts and mixtures thereof.

(ii) Non-ionic surfactant(s):

The non-ionic surface-active agents themselves are also compounds which are well known per se (in this respect see in particular the "Handbook of Surfactants" by M. R. Porter, published by Blackie & Son (Glasgow and London), 1991, pp. 116–178) and, in the context of the present invention, their nature does not assume any critical character. They can thus be chosen especially from (nonlimiting list) polyethoxylated, polypropoxylated or polyglycerolated fatty alcohols, alpha-diols, alkylphenols or acids, which have a fatty chain containing, for example, 8 to 18 carbon atoms, it being possible for the number of ethylene oxide or propylene oxide groups to range especially from 2 to 50 and it being possible for the number of glycerol groups to range especially from 2 to 30. Mention may also be made of the copolymers of ethylene and propylene oxide, the condensates of ethylene and propylene oxide with fatty alcohols; the polyethoxylated fatty amides preferably having from 2 to 30 mol of ethylene oxide, the polyglycerolated fatty amides on average containing 1 to 5 glycerol groups and in particular 1.5 to 4; the polyethoxylated fatty amines preferably having 2 to 30 mol of ethylene oxide; the oxyethylenated esters of sorbitan fatty acids having from 2 to 30 mol of ethylene oxide; the sucrose esters of fatty acids, the polyethylene glycol esters of fatty acids, alkylpolyglycosides, the N-alkylglucamine derivatives, amine oxides such as the oxides of ($C_{10}$–$C_{14}$)alkylamines or the N-acylaminopropylmorpholine oxides. It will be noted that alkylpolyglycosides constitute non-ionic surfactants which enter particularly well into the scope of the present invention.

(iii) Amphoteric surfactant(s):

The amphoteric surface-active agents, the nature of which does not assume any critical character in the context of the present invention, may be especially (nonlimiting list) derivatives of aliphatic secondary or tertiary amines in which the aliphatic radical is a linear or branched chain containing 8 to 22 carbon atoms and containing at least one water-solubilizing anionic group (for example carboxylate, sulphonate, sulphate, phosphate or phosphonate); ($C_8$–$C_{20}$) alkylbetaines, sulphobetaines, ($C_8$–$C_{20}$)alkylamido($C_1$–$C_6$) alkylbetaines or ($C_8$–$C_{20}$)alkylamido($C_1$–$C_6$) alkylsulphobetaines may further be mentioned.

Among the amine derivatives, there may be mentioned products sold under the name Miranol, as described in U.S. Pat. No. 2,528,378 and U.S. Pat. No. 2,781,354 and with structures:

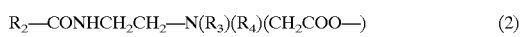
(2)

in which: $R_2$ denotes an alkyl radical derived from an acid $R_2$—COOH present in hydrolysed copra oil, a heptyl, nonyl or undecyl radical, $R_3$ denotes a beta-hydroxyethyl group and $R_4$ a carboxymethyl group; and

(3)

in which:
B represents —$CH_2CH_2OX'$, C represents —$(CH_2)_z$—Y', with z =1 or 2,
X' denotes the —$CH_2CH_2$—COOH group or a hydrogen atom
Y' denotes —COOH or the radical —$CH_2$—CHOH—$SO_3H$
$R_2$, denotes an alkyl radical of an acid $R_9$—COOH present in copra oil or in hydrolysed linseed oil, an alkyl radical, in particular $C_7$, $C_9$, $C_{11}$ or $C_{13}$, a $C_{17}$ alkyl radical and its iso form or an unsaturated radical $C_{17}$.

These compounds are classified in the CTFA dictionary, 5th Edition, 1993, under the names Disodium Cocoamphodiacetate, Disodium Lauroamphodiacetate, Disodium Caprylamphodiacetate, Disodium Capryloamphodiacetate, Disodium Cocoamphodipropionate, Disodium Lauroamphodipropionate, Disodium Caprylamphodipropionate, Disodium Capryloamphodipropionate, Lauroamphodipropionic acid and Cocoamphodipropionic acid. By way of example, there may be mentioned the cocoamphodiacetate sold under the trade name Miranol C2M concentrated by the company Rhône-Poulenc.

In the compositions in accordance with the invention, use is preferably made of mixtures of surface-active agents and in particular mixtures of anionic surface-active agents and of amphoteric or non-ionic surface-active agents. A particularly preferred mixture is a mixture composed of at least one anionic surface-active agent and of at least one amphoteric surface-active agent.

Use is preferably made of an anionic surface-active agent chosen from sodium, triethanolamine or ammonium ($C_{12}$–$C_{14}$)alkyl sulphates, sodium ($C_{12}$–$C_{14}$)alkyl ether sulphates oxyethylenated with 2.2 mol of ethylene oxide, sodium cocoylisethionate and sodium alpha-($C_{14}$–$C_{16}$) olefinsulphonate and mixtures thereof with:

either an amphoteric surface-active agent, such as the amine derivatives named disodium cocoamphodipropionate or sodium cocoamphopropionate sold in particular by the company Rhône-Poulenc under the trade name "Miranol C2M Conc" as an aqueous solution containing 38% of active material or under the name Miranol C32;

or an amphoteric surface-active agent of zwitterionic type, such as alkylbetaines, in particular the cocoylbetaine sold under the name "Dehyton AB 30", as an aqueous solution containing 32% of AM by the company Henkel.

(iv) Cationic surfactants:

Among the cationic surfactants, there may be mentioned in particular (nonlimiting list): the salts of optionally polyoxyalkylenated primary, secondary or tertiary fatty amines; quaternary ammonium salts, such as tetraalkyammonium, alkylamidoalkyltrialkylammonium, trialkylbenzylammonium, trialkylhydroxyalkylammonium or alkylpyridinium chlorides or bromides; imidazoline derivatives; or amine oxides of cationic nature. It will be noted that the cationic surfactants, the use of which is not ruled out, do not constitute preferred surfactants for making use of the present invention.

B—CONDITIONING SYSTEM

The compositions according to the invention necessarily comprise, as conditioning system, an oil-in-water emulsion having oil globules with a mean size of less than 150 nm and comprising an amphiphilic lipid phase, characterized in that the amphiphilic lipid phase comprises at least one non-ionic amphiphilic lipid which is liquid at an ambient temperature of less than 45° C.

The non-ionic amphiphilic lipids of the invention are preferentially chosen from silicone surfactants and esters of at least one polyol chosen from the group formed by polyethylene glycol containing from 1 to 60 ethylene oxide units, sorbitan, glycerol containing from 2 to 30 ethylene oxide units or polyglycerols containing from 2 to 15 glycerol units and of at least one fatty acid containing at least one saturated or unsaturated, linear or branched, $C_8$–$C_{22}$ alkyl chain. It is also possible to use mixtures of the above compounds.

The silicone surfactants which can be used according to the present invention are silicone compounds containing at least one oxyethylenated —$OCH_2CH_2$— and/or oxypropylenated —$OCH_2CH_2CH_2$— chain. Mention may be made, as silicone surfactants which can be used according to the present invention, of those described in the documents U.S. Pat. No. 5,364,633 and U.S. Pat. No. 5,411,744.

The silicone surfactant used according to the present invention is preferably a compound of formula (I):

$$R_1-\underset{\underset{CH_3}{|}}{\overset{\overset{CH_3}{|}}{Si}}O-[\underset{\underset{CH_3}{|}}{\overset{\overset{CH_3}{|}}{Si}}O]_A-[\underset{\underset{R_2}{|}}{\overset{\overset{CH_3}{|}}{Si}}O]_B-\underset{\underset{CH_3}{|}}{\overset{\overset{CH_3}{|}}{Si}}-R_3 \quad (I)$$

in which: $R_1$, $R_2$ and $R_3$, independently of one another, represent a $C_1$–$C_6$ alkyl radical or a —$(CH_2)_x$—$(OCH_2CH_2)_y$—$(OCH_2CH_2CH_2)_z$—$OR_4$ radical, at least one $R_1$, $R_2$ or $R_3$ radical not being an alkyl radical, $R_4$ being a hydrogen, an alkyl radical or an acyl radical;
A is an integer ranging from 0 to 200;
B is an integer ranging from 0 to 50; provided that A and B are not simultaneously equal to zero;
x is an integer ranging from 1 to 6;
y is an integer ranging from 1 to 30;
z is an integer ranging from 0 to 5.

According to a preferred embodiment of the invention, in the compound of formula (I), the alkyl radical is a methyl radical, x is an integer ranging from 2 to 6 and y is an integer ranging from 4 to 30.

Mention may be made, as example of silicone surfactants of formula (I), of the compounds of formula (II):

$$(CH_3)_3SiO-[(CH_3)_2SiO]_A-(CH_3\underset{\underset{(CH_2)_2-(OCH_2CH_2)_y-OH}{|}}{Si}O)_B-Si(CH_3)_3 \quad (II)$$

in which A is an integer ranging from 20 to 105, B is an integer ranging from 2 to 10 and y is an integer ranging from 10 to 20.

Mention may also be made, as example of silicone surfactants of formula (I), of the compounds of formula (III):

$$HO-(OCH_2CH_2)_y-(CH_2)_3-[(CH_3)_2SiO]_{A'}-(CH_2)_3-(OCH_2CH_2)_y-OH \quad (III)$$

in which A' and y are integers ranging from 10 to 20.

It is possible to use, as compounds of the invention, those sold by the company Dow Corning under the names DC 5329, DC 7439-146, DC 2-5695 and Q4-3667. The compounds DC 5329, DC 7439-146 and DC 2-5695 are compounds of formula (II) where, respectively, A is 22, B is 2 and y is 12; A is 103, B is 10 and y is 12; and A is 27, B is 3 and y is 12.

The compound Q4-3667 is a compound of formula (III) where A is 15 and y is 13.

Mention may more particularly be made, among non-ionic amphiphilic lipids, by way of example, of:
polyethylene glycol isostearate, the glycol having a molecular weight of 400,
diglyceryl isostearate,
polyglycerol laurate containing 10 glycerol units,
sorbitan oleate,
sorbitan isostearate,
α-butylglucoside cocoate or α-butylglucoside caprate.

The ratio by weight of the amount of oil contained in the emulsion in accordance with the invention to the amount of the amphiphilic lipid phase preferably varies from 2 to 10 and more preferentially from 3 to 6.

A specific form of emulsion in accordance with the invention is characterized in that the amphiphilic lipid phase additionally comprises one or more ionic amphiphilic lipids.

The ionic amphiphilic lipids used in the nanoemulsions of the invention are preferably chosen from the group formed by anionic lipids, amphoteric lipids and cationic lipids and mixtures thereof.

The anionic amphiphilic lipids are more particularly chosen from the group formed by:
alkaline salts of dicetyl and dimyristyl phosphate;
alkaline salts of cholesterol sulphate;
alkaline salts of cholesterol phosphate;
lipoamino acids, such as mono- and disodium acylglutamates;
sodium salts of phosphatidic acid;
phospholipids;
alkylsulphonic derivatives, such as those of formula:

$$R-\underset{\underset{SO_3M}{|}}{CH}-CO-O-(CH_2-CH_2-CO)-CH_3$$

in which R represents $C_{16}$–$C_{22}$ alkyl radicals, in particular $C_{16}H_{33}$ and $C_{18}H_{37}$ radicals, taken as a mixture or separately, and M is an alkali metal, such as sodium.

The cationic amphiphilic lipids used in the nanoemulsions of the invention are preferably chosen from the group formed by quaternary ammonium salts, fatty amines and salts thereof.

The quaternary ammonium salts are, for example:
those which exhibit the following general formula (VIII):

$$\left[\begin{array}{c}R_1\diagdown\phantom{N}\diagup R_3\\ N \\ R_2\diagup\phantom{N}\diagdown R_4\end{array}\right]^+ X^- \quad (VIII)$$

in which the $R_1$ to $R_4$ radicals, which can be identical or different, represent a linear or branched aliphatic radical containing from 1 to 30 carbon atoms, or an aromatic radical, such as aryl or alkylaryl. The aliphatic radicals can contain heteroatoms, such as, in particular, oxygen, nitrogen, sulphur or halogens. The aliphatic radicals are, for example, chosen from alkyl, alkoxy, polyoxy($C_2$–$C_6$)alkylene, alkylamide, ($C_{12}$–$C_{22}$) alkylamido($C_2$–$C_6$)alkyl, ($Cl_2$–$C_{22}$) alkyl acetate or hydroxyalkyl radicals containing approximately from 1 to 30 carbon atoms; X is an anion chosen from the group of the halides, phosphates, acetates, lactates, ($C_2$–$C_6$)alkyl sulphates, or alkyl- or alkylarylsulphonates, imidazolinium quaternary ammonium salts, such as, for example, that of following formula (IX):

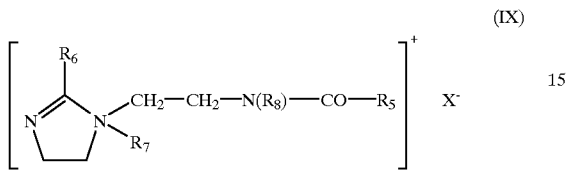

(IX)

in which $R_5$ represents an alkenyl or alkyl radical containing from 8 to 30 carbon atoms, for example derivatives of tallow fatty acids, $R_6$ represents a hydrogen atom, a $C_1$–$C_4$ alkyl radical or an alkenyl or alkyl radical containing from 8 to 30 carbon atoms, $R_7$ represents a $C_1$–$C_4$ alkyl radical, $R_8$ represents a hydrogen atom or a $C_1$–$C_4$ alkyl radical and X is an anion chosen from the group of the halides, phosphates, acetates, lactates, alkyl sulphates, or alkyl- or alkylarylsulphonates. $R_5$ and $R_6$ preferably denote a mixture of alkenyl or alkyl radicals containing from 12 to 21 carbon atoms, for example derivatives of tallow fatty acids, $R_7$ preferably denotes methyl and R8 preferably denotes hydrogen. Such a product is, for example, sold under the name "Rewoquat W 75" by the company Rewo, quaternary diammonium salts of formula (X):

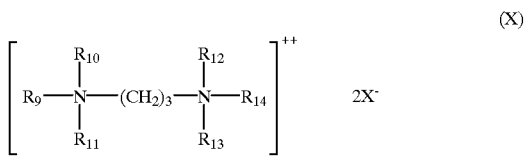

(X)

in which $R_9$ denotes an aliphatic radical containing approximately from 16 to 30 carbon atoms, $R_{10}$, $R_{11}$, $R_{12}$, $R_{13}$ and $R_{14}$, which are identical or different, are chosen from hydrogen or an alkyl radical containing from 1 to 4 carbon atoms and X is an anion chosen from the group of the halides, acetates, phosphates, nitrates and methyl sulphates. Such quaternary diammonium salts comprise in particular propanetallowdiammonium dichloride, quaternary ammonium salts containing at least one ester functional group.

The quaternary ammonium salts containing at least one ester functional group which can be used according to the invention are, for example, those of following formula (XI):

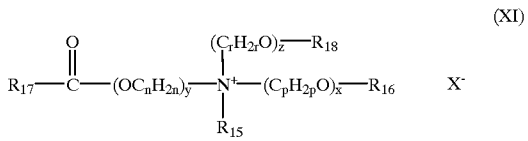

(XI)

in which:
$R_{15}$ is chosen from $C_1$–$C_6$ alkyl radicals and $C_1$–$C_6$ hydroxyalkyl or dihydroxyalkyl radicals;

$R_{16}$ is chosen from:
the

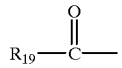

radical,
saturated or unsaturated, linear or branched, $C_1C_{22}$ hydrocarbon radicals $R_{20}$,
the hydrogen atom, $R_{18}$ is chosen from:
the

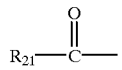

radical,
saturated or unsaturated, linear or branched, $C_{1-C6}$ hydrocarbon radicals $R_{22}$,
the hydrogen atom, $R_{17}$, $R_{19}$ and $R_{21}$, which are identical or different, are chosen from saturated or unsaturated, linear or branched, $C_7$–$C_{21}$ hydrocarbon radicals;

n, p and r, which are identical or different, are integers having values from 2 to 6;

y is an integer having a value from 1 to 10;

x and z, which are identical or different, are integers having values from 0 to 10;

X is an organic or inorganic, simple or complex anion;

with the proviso that the sum x+y+z has a value from 1 to 15, that when x has a value of 0, then $R_{16}$ denotes $R_{20}$, and that when z has a value of 0, then $R_{18}$ denotes $R_{22}$.

The $R_{15}$ alkyl radicals can be linear or branched and more particularly linear.

$R_{15}$ preferably denotes a methyl, ethyl, hydroxyethyl or dihydroxypropyl radical and more particularly a methyl or ethyl radical.

The sum x+y+z advantageously has a value from 1 to 10.

When $R_{16}$ is an $R_{20}$ hydrocarbon radical, it can be long and have from 12 to 22 carbon atoms or short and have from 1 to 3 carbon atoms.

When $R_{17}$ is an $R_{22}$ hydrocarbon radical, it preferably has 1 to 3 carbon atoms.

$R_{17}$, $RL_{19}$ and $R_{21}$, which are identical or different, are advantageously chosen from saturated or unsaturated, linear or branched, $C_{11}$–$C_{21}$ hydrocarbon radicals and more particularly from saturated or unsaturated, linear or branched, $C_{11}$–$C_{21}$ alkyl and alkenyl radicals.

Preferably, x and z, which are identical or different, have the value 0 or 1. Advantageously, y is equal to 1. Preferably, n, p and r, which are identical or different, have a value of 2 or 3 and, more particularly still, are equal to 2.

The anion is preferably a halide (chloride, bromide or iodide) or an alkyl sulphate, more particularly methyl sulphate. However, it is possible to use methanesulphonate, phosphate, nitrate, tosylate, an anion derived from organic acid, such as acetate or lactate, or any other anion compatible with ammonium containing an ester functional group.

The X anion is more particularly still chloride or methyl sulphate.

Use is more particularly made of the ammonium salts of formula (XI) in which:

$R_{15}$ denotes a methyl or ethyl radical, x and y are equal to 1;

z is equal to 0 or 1;

n, p and r are equal to 2;

$R_{16}$ is chosen from:
the

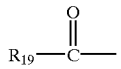

radical methyl, ethyl or $C_{14}$–$C_{22}$ hydrocarbon radicals
the hydrogen atom;

$R_{18}$ is chosen from:
the

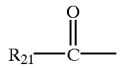

radical
the hydrogen atom;

$R_{17}$, $R_{19}$ and $R_{21}$, which are identical or different, are chosen from saturated or unsaturated, linear or branched, C13–$C_{17}$ hydrocarbon radicals and preferably from saturated or unsaturated, linear or branched, $C_{13}$–$C_{17}$ alkyl and alkenyl radicals. The hydrocarbon radicals are advantageously linear.

Mention may be made, for example, of the compounds of formula (XI), such as diacyloxyethyldimethylammonium, diacyloxyethyl(hydroxyethyl)methylammonium, monoacyloxyethyl(dihydroxyethyl)methylammonium, triacyloxyethyl (methyl)ammonium or monoacyloxyethyl (hydroxyethyl)dimethylammonium salts (chloride or methyl sulphate, in particular) and mixtures thereof. The acyl radicals preferably have 14 to 18 carbon atoms and more particularly originate from a vegetable oil, such as palm oil or sunflower oil. When the compound contains several acyl radicals, the latter can be identical or different.

These products are obtained, for example, by direct esterification of triethanolamine, of triisopropanolamine, of alkyldiethanolamine or of alkyldiisopropanolamine, which are optionally oxyalkylenated, with fatty acids or mixtures of fatty acids of vegetable or animal origin or by transesterification of their methyl esters. This esterification is followed by a quaternization using an alkylating agent, such as an alkyl (methyl or ethyl preferably) halide, a dialkyl (methyl or ethyl preferably) sulphate, methyl methanesulphonate, methyl para-toluenesulphonate, or glycol or glycerol chlorohydrin.

Such compounds are, for example, sold under the names Dehyquart by the company Henkel, Stepanquat by the company Stepan, Noxamium by the company Ceca or Rewoquat WE 18 by the company Rewo-Witco.

The composition according to the invention preferably contains a mixture of quaternary ammonium mono-, di- and triester salts, with a majority by weight of diester salts.

Use may be made, as mixture of ammonium salts, of, for example, the mixture containing 15 to 30% by weight of acyloxyethyl(dihydroxyethyl)methylammonium methyl sulphate, 45 to 60% of diacyloxyethyl(hydroxyethyl) methylammonium methyl sulphate and 15 to 30% of triacyloxyethyl(methyl)ammonium methyl sulphate, the acyl radicals having from 14 to 18 carbon atoms and originating from optionally partially hydrogenated palm oil.

It is also possible to use the ammonium salts containing at least one ester functional group described in U.S. Pat. No. 4,874,554 and U.S. Pat. No. 4,137,180.

Preference is given, among the quaternary ammonium salts of formula (VIII), to, on the one hand, tetraalkylammonium chlorides, such as, for example, dialkyldimethylammonium or alkyltrimethylammonium chlorides in which the alkyl radical contains approximately from 12 to 22 carbon atoms, in particular behenyltrimethylammonium, distearyldimethylammonium, cetyltrimethylammonium and benzyldimethylstearyl-ammonium chlorides, or alternatively, on the other hand, stearamidopropyldimethyl (myristyl acetate)ammonium chloride sold under the name "Ceraphyl 70" by the company Van Dyk.

According to the invention, behenyltrimethylammonium chloride is the most particularly preferred quaternary ammonium salt.

The amphiphilic ionic lipids are present in the nanoemulsions of the invention preferably in concentrations ranging from 0 to 60% by weight and more particularly from 10 to 50% by weight with respect to the total weight of the amphiphilic lipid phase.

The nanoemulsions in accordance with the invention contain an amount of oil ranging preferably from 5 to 40% by weight with respect to the total weight of the emulsion and preferably from 10 to 30% by weight.

The oils which can be used in the emulsions of the invention are preferably chosen from the group formed by:

animal or vegetable oils formed by esters of fatty acids and of polyols, in particular liquid triglycerides, for example sunflower, avocado, maize, soybean, gourd, grape seed, sesame and hazelnut oils, fish oils or glycerol tricaprocaprylate, or vegetable or animal oils of formula $R_9COOR_{10}$, in which $R_9$ represents the residue of a higher fatty acid containing from 7 to 29 carbon atoms and $R_1O$ represents a branched hydrocarbon chain containing from 3 to 30 carbon atoms, for example Purcellin oil;

natural or synthetic essential oils, such as, for example, eucalyptus, lavandin, lavender, vetiver, litsea cubeba, lemon; santal, rosemary, camomile, savory, nutmeg, cinnamon, hyssop, caraway, orange, geraniol, cade and bergamot oils;

hydrocarbons, such as hexadecane and liquid paraffin;

halocarbons, in particular fluorocarbons, such as fluoroamines, for example perfluorotributylamine, fluorinated hydrocarbons, for example perfluorodecahydronaphthalene, fluoroesters and fluoroethers;

esters of an inorganic acid and of an alcohol;

ethers and polyethers;

silicones as a mixture with at least one of the oils defined above, for example decamethylcyclopentasiloxane or dodecamethylcyclohexasiloxane.

The mean size of the oil globules is generally between 30 and 150 nm, preferably between 40 and 100 nm and more particularly still between 50 and 80 nm.

The compositions of the invention can contain water-soluble or fat-soluble active ingredients having a cosmetic or dermopharmaceutical activity. The fat-soluble active ingredients are in the oily globules of the emulsion, whereas the water-soluble active ingredients are in the aqueous phase of the emulsion. Mention may be made, as examples of active ingredient, of vitamins, such as vitamin E and its derivatives, provitamins, such as panthenol, moisturizers, ceramides, pseudoceramides and sunscreening agents.

The compositions according to the invention generally contain an emulsion as defined above in concentrations of between 2 and 50% by weight with respect to the total weight of the composition.

The oil or oils can be used in the compositions in accordance with the invention in concentrations generally of between 0.1 and 15% and preferably between 0.2 and 10% by weight with respect to the total weight of the composition.

The cosmetically acceptable aqueous medium can be composed solely of water or of a mixture of water and of a cosmetically acceptable solvent, such as a lower $C_1$–$C_4$ alcohol, such as ethanol, isopropanol, tert-butanol or n-butanol; alkylene glycols, such as propylene glycol, or glycol ethers.

The detergent compositions according to the invention exhibit a final pH generally of between 3 and 10. This pH is preferably between 5 and 8. The pH can be conventionally adjusted to the desired value by addition of a base (organic or inorganic) to the composition, for example aqueous ammonia or a primary, secondary or tertiary (poly)amine, such as monoethanolamine, diethanolamine, triethanolamine, isopropanolamine or 1,3-propanediamine, or alternatively by addition of an acid, preferably a carboxylic acid, such as, for example, citric acid.

The compositions in accordance with the invention can contain, in addition to the combination defined above, viscosity regulating agents, such as electrolytes, or thickening agents. Mention may in particular be made of sodium chloride, sodium xylenesulphonate, scleroglucans, xanthan gums, fatty acid alkanolamides, alkyl ether carboxylic acid alkanolamides optionally oxyethylenated with up to 5 mol of ethylene oxide, such as the product sold under the name "Aminol A15" by the company Chem Y, crosslinked poly (acrylic acid)s and crosslinked acrylic acid/$C_{10}$–$C_{30}$ alkyl acrylate copolymers. These viscosity regulating agents are used in the compositions according to the invention in proportions which can range up to 10% by weight with respect to the total weight of the composition.

The compositions in accordance with the invention can also contain up to 5% of pearlescent or opacifying agents well known in the state of the art, such as, for example, sodium or magnesium palmitates, sodium or magnesium stearates and hydroxystearates, or acylated derivatives containing a fatty chain, such as ethylene glycol or polyethylene glycol monostearates or distearates.

The compositions in accordance with the invention can in addition optionally contain other agents having the effect of improving the cosmetic properties of hair or of the skin without, however, detrimentally affecting the stability of the compositions. Mention may be made, in this respect, of cationic surface-active agents, anionic or non-ionic or cationic or amphoteric polymers, proteins, protein hydrolysates, ceramides, pseudoceramides, fatty acids containing linear or branched $C_6$–$C_{40}$ chains, such as 18-methyleicosanoic acid, hydroxy acids, vitamins, panthenol, volatile or non-volatile silicones, which are soluble and insoluble in the medium, and mixtures thereof.

The conditioning agents of cationic polymer type which can be used in accordance with the present invention can be chosen from all those already known per se as improving the cosmetic properties of hair treated with detergent compositions, namely, in particular, those described in Patent Application EP-A-0,337,354 and in French Patent Applications FR-A-2,270,846, 2,383,660, 2,598,611, 2,470,596 and 2,519,863.

In a still more general way, within the meaning of the present invention, the expression "cationic polymer" denotes any polymer containing cationic groups and/or groups which can be ionized to cationic groups.

Among all the cationic polymers capable of being used in the context of the present invention, preference is given to the employment of quaternary derivatives of cellulose ether, such as the products sold under the name "JR 400" by the company Union Carbide Corporation, cyclopolymers, in particular diallyldimethylammonium salt homopolymers and copolymers of diallyldimethylammonium salt and of acrylamide, in particular the chlorides, sold under the names "Merquat 100", "Merquat 550" and "Merquat S" by the company Merck, or cationic polysaccharides and more particularly guar gums modified by 2,3-epoxypropyltrimethylammonium chloride, sold, for example, under the name "Jaguar C13S" by the company Meyhall.

According to the invention, the cationic polymer or polymers can represent from 0.001% to 10% by weight, preferably from 0.005% to 5% by weight and, more preferentially still, from 0.01% to 3% by weight of the total weight of the final composition.

The compositions according to the invention can also contain foam synergists, such as $C_{10}$–$C_{18}$ 1,2-alkanediols or fatty alkanolamides derived from mono- or from diethanolamine.

Of course, a person skilled in the art will take care to choose this or these possible additional compounds and/or their amounts so that the advantageous properties intrinsically attached to the combination (washing base + oil nanoemulsion) in accordance with the invention are not, or not substantially, detrimentally affected by the envisaged addition or additions.

These compositions can be provided in the form of more or less thickened liquids, of creams or of gels and they are mainly suitable for washing or caring for the hair.

When the compositions in accordance with the invention are employed as conventional shampoos, they are simply applied to wet hair and the foam generated by massaging or rubbing with the hands is then removed, after an optional period of rest, by rinsing with water, it being possible for the operation to be repeated one or more times.

Another subject of the invention is a process for washing and for conditioning keratinous substances, such as, in particular, hair, which consists in applying, to the said wetted substances, an effective amount of a composition as defined above and in then rinsing with water, after an optional period of rest.

The compositions according to the invention are preferably used as shampoos for washing and conditioning the hair and they are applied, in that case, to wet hair in amounts which are effective for washing them, this application being followed by rinsing with water.

The compositions in accordance with the invention can also be used as shower gels for washing and conditioning the hair and/or the skin, in which case they are applied to the wet skin and/or hair and are rinsed after application.

Concrete but in no way limiting examples illustrating the invention will now be given.

EXAMPLE

Two shampoo compositions were produced, one in accordance with the invention (composition A) and the other comparative (composition B):

|  | A<br>Invention | B<br>Comparative |
| --- | --- | --- |
| Sodium lauryl ether sulphate (70/30 $C_{12}/C_{14}$) containing 2.2 mol of ethylene oxide as an aqueous solution with an AM content of 28% (AM = active material) | 15 g AM | 15 g AM |
| Cocoylbetaine (Dehyton AB 30) | 2.7 g AM | 2.7 g AM |
| Nanoemulsion (*) | 15 g (3 g of avocado oil) | — |
| Emulsion (**) | — | 15 g (3 g of avocado oil) |
| Fragrance, preservative | q.s. | q.s. |
| Citric acid q.s. pH | 7.6 | 7.6 |
| Demineralized water q.s. | 100 g | 100 g |

(*) Nanoemulsion

The nanoemulsion is prepared according to the following procedure:
in a first phase, the amphiphilic lipids are homogenized with the oils and the lipophilic active ingredients and adjuvants at a temperature of 45° C.;
in a second phase, the hydrophilic active ingredients and adjuvants are dissolved at a temperature of 20 to 30° C.;
the two phases are then mixed using a propeller homogenizer and then homogenization is carried out using a high pressure homogenizer of the Soavi-Niro type at a pressure of 1500 bars, with 7 passages, the temperature of the product being maintained below 35° C.

| First Phase: | |
| --- | --- |
| PEG-400 isostearate, sold by the company Unichema | 4.5% |
| disodium salt of N-stearoyl-L-glutamic acid, sold under the name Acylglutamate HS21 by the company Ajinomoto (ionic amphiphilic lipid) | 0.5% |
| Avocado oil | 20% |
| Non-denatured absolute ethanol | 15% |
| Second phase: | |
| Glycerol | 5% |
| Demineralized water | q.s. for 100% |

The size of the oil globules is approximately 60 nm.
(**) Emulsion
The emulsion contains the same compounds as the nanoemulsion but the preparation is carried out according to a conventional procedure. The size of the oil globules is approximately 1500 nm.

The shampoo compositions are prepared by mixing the emulsion or the nanoemulsion with the other constituents of the shampoo at room temperature.

The composition B is unstable and the oil separates out at the surface of the liquid, whereas the composition A is homogeneous and stable.

The composition B exhibits an insufficient foaming power, whereas the composition A according to the invention exhibits an excellent foaming power.

Shampooing was carried out by applying approximately 12 g of the composition A to sensitive hair which had been wetted beforehand. The shampoo is made to foam and then copious rinsing is carried out with water. The same procedure is carried out as above with the comparative composition B.

A panel of experts evaluated the appearance of the dried hair.

All the experts indicate that hair treated with the composition A according to the invention is highly individualized and non-sticky, whereas hair treated with the composition B has a dirty and greasy appearance.

What is claimed is:
1. A detergent and conditioning composition comprising:
(A) a washing base, wherein said washing base comprises at least one surfactant chosen from
anionic surfactants chosen from
the salts of alkyl sulphates, alkyl ether sulphates, alkylamido ether sulphates, alkylarylpolyether sulphates, monoglyceride sulphates, alkylsulphonates, alkyl phosphates, alkylamidesulphonates, alkylarylsulphonates, α-olefinsulphonates, paraffinsulphonates, alkyl sulphosuccinates, alkyl ether sulphosuccinates, alkylamidesulphosuccinates, alkyl sulphosuccinamates, alkyl sulphoacetates, alkyl ether phosphates, acylsarcosinates, acylisethionates and N-acyltaurates;
alkyl-D-galactosideuronic acids, polyoxyalkylenated ($C_6$–$C_{24}$)alkyl ether carboxylic acids, polyoxyalkylenated ($C_6$–$C_{24}$)alkylaryl ether carboxylic acids, polyoxyalkylenated ($C_6$–$C_{24}$)alkylamido ether carboxylic acids and salts thereof;
the salts of fatty acids chosen from oleic, ricinoleic, palmitic and stearic acids, the acids of copra oil, the acids of hydrogenated copra oil, and the salts of acyl-lactylates in which the acyl radical contains 8 to 20 carbon atoms;
nonionic surfactants chosen from
polyethoxylated, polypropoxylated and polyglycerolated fatty alcohols, alphadiols, alkylphenols and acids, having a fatty chain;
copolymers of ethylene and propylene oxide and the condensates of ethylene and propylene oxide with fatty alcohols;
polyethoxylated fatty amides, polyglycerolated fatty amides, oxyethylenated esters of sorbitan fatty acids, sucrose esters of fatty acids, alkylpolyglycosides, polyethylene glycol esters of fatty acids, N-alkylglucamine derivatives, and amine oxides;
amphoteric surfactants chosen from
derivatives of aliphatic secondary or tertiary amines containing at least one water-solubizing anionic group and further wherein said aliphatic radical contains 8 to 22 carbon atoms; ($C_8$–$C_{20}$)alkylbetaines, sulphobetaines, ($C_8$–$C_{20}$)alkylamido($C_1$–$C_6$)alkylbetaines, and ($C_8$–$C_{20}$)alkylamido($C_1$–$C_6$)alkylsulphobetaines; and
cationic surfactants chosen from
the salts of optionally polyoxyalkylenated primary, secondary and tertiary fatty amines, quaternary ammonium salts, imidazoline derivatives, and amine oxides of cationic nature;
and
(B) a conditioning system comprising at least one oil-in-water emulsion having oil globules with a mean size of less than 150 nm and comprising an amphiphilic lipid phase, said amphiphilic lipid phase comprising at least one non-ionic amphiphilic lipid which is liquid at a temperature of less than 45° C.

2. The composition according to claim 1, wherein said washing base is an aqueous washing base and wherein said composition further comprises a cosmetically appropriate medium.

3. The composition according to claim 1, wherein said washing base represents from 4% to 50% by weight of the total weight of the composition.

4. The composition according to claim 3, wherein said washing base represents from 10% to 35% by weight of the total weight of the composition.

5. The composition according to claim 4, wherein said washing base represents from 12% to 25% by weight of the total weight of the composition.

6. The composition according to claim 1, wherein said salts of alkyl sulphates, alkyl ether sulphates, alkylamido ether sulphates, alkylarylpolyether sulphates, monoglyceride sulphates, alkylsulphonates, alkyl phosphates, alkylamidesulphonates, alkylarylsulphonates, α-olefinsulphonates, paraffinsulphonates, alkyl sulphosuccinates, alkyl ether sulphosuccinates, alkylamidesulphosuccinates, alkyl sulphosuccinamates, alkyl sulphoacetates, alkyl ether phosphates, acylsarcosinates, acylisethionates and N-acyltaurates are chosen from alkali metal salts, ammonium salts, amine salts, aminoalcohol salts and magnesium salts.

7. The composition according to claim 1, wherein said alkyl and acyl portions of said salts of alkyl sulphates, alkyl ether sulphates, alkylamido ether sulphates, alkylarylpolyether sulphates, monoglyceride sulphates, alkylsulphonates, alkyl phosphates, alkylamidesulphonates, alkylarylsulphonates, α-olefinsulphonates, paraffinsulphonates, alkyl sulphosuccinates, alkyl ether sulphosuccinates, alkylamidesulphosuccinates, alkyl sulphosuccinamates, alkyl sulphoacetates, alkyl ether phosphates, acylsarcosinates, acylisethionates and N-acyltaurates contain from 12 to 20 carbon atoms, and said aryl portions are chosen from phenyl and benzyl groups.

8. The composition according to claim 1, wherein said anionic surfactants are chosen from alkyl sulphate and alkyl ether sulphate salts.

9. The composition according to claim 1, wherein said fatty chain of said polyethoxylated, polypropoxylated and polyglycerolated fatty acids contains from 8 to 18 carbon atoms.

10. The composition according to claim 1, wherein said aliphatic secondary and tertiary amines are chosen from:

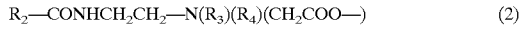

$$R_2-CONHCH_2CH_2-N(R_3)(R_4)(CH_2COO-) \quad (2)$$

in which

R$_2$ is chosen from an alkyl radical derived from an acid R$_2$—COOH present in hydrolysed copra oil, a heptyl radical, a nonyl radical and an undecyl radical, R$_3$ denotes a beta-hydroxyethyl group and R$_4$ denotes a carboxymethyl group;

and

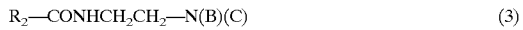

$$R_2-CONHCH_2CH_2-N(B)(C) \quad (3)$$

in which:

B represents —CH$_2$CH$_2$OX',

C represents —(CH$_2$)$_z$—Y', with z=1 or 2,

X' is chosen from the —CH$_2$CH$_2$—COOH group and a hydrogen atom

Y' is chosen from —COOH and the radical —CH$_2$—CHOH—SO$_3$H, and

R$_2$ denotes and alkyl radical.

11. The composition according to claim 1, wherein said at least one non-ionic amphiphilic lipid is chosen from silicone surfactants and esters of:

at least one polyol chosen from polyethylene glycols containing from 1 to 60 ethylene oxide units, sorbitan, glycerols containing from 2 to 30 ethylene oxide units, and polyglycerols containing from 2 to 15 glycerol units, and at least one fatty acid containing at least one saturated or unsaturated, linear or branched, C$_8$–C$_{22}$ alkyl chain.

12. The composition according to claim 11, wherein said silicone surfactants are chosen from silicone compounds containing at least one chain chosen from oxyethylenated —OCH$_2$CH$_2$— and oxypropylenated —OCH$_2$CH$_2$CH$_2$— chains.

13. The composition according to claim 11, wherein said silicone surfactants are chosen from compounds of formula (I):

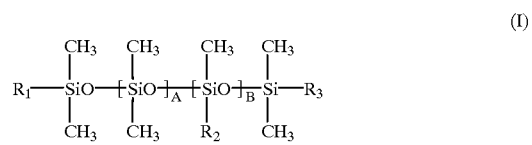

in which:

R$_1$, R$_2$ and R$_3$, independently are chosen from C$_1$–C$_6$ alkyl radicals and —(CH$_2$)$_x$—(OCH$_2$CH$_2$)$_y$—(OCH$_2$CH$_2$CH$_2$)$_z$—OR$_4$ radicals, at least one R$_1$, R$_2$ or R$_3$ radical not being an alkyl radical, and wherein R$_4$ is chosen from a hydrogen atom, an alkyl radical and an acyl radical;

A is an integer ranging from 0 to 200;

B is an integer ranging from 0 to 50; provided that A and B are not simultaneously equal to zero;

x is an integer ranging from 1 to 6;

y is an integer ranging from 1 to 30; and z is an integer ranging from 0 to 5.

14. The composition according to claim 11, wherein said silicone surfactants are chosen from compounds of formula (II):

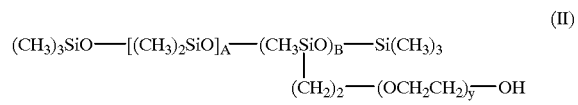

in which

A is an integer ranging from 20 to 105, B is an integer ranging from 2 to 10 and y is an integer ranging from 10 to 20.

15. The composition according to claim 11, wherein said silicone surfactants are chosen from compounds of formula (III):

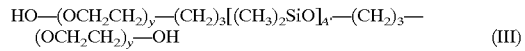

in which

A' and y are integers ranging from 10 to 20.

16. The composition according to claim 1, wherein said at least one non-ionic amphiphilic lipid is chosen from polyethylene glycol isostearate, the glycol having a molecular weight of 400, diglyceryl isostearate, polyglycerol laurate containing 10 glycerol units, sorbitan oleate, sorbitan isostearate, α-butylglucoside cocoate and α-butylglucoside caprate.

17. The composition according to claim 1, wherein the ratio by weight of the amount of oil contained in the emulsion to the amount of the amphiphilic lipid phase ranges from 2:1 to 10:1.

18. The composition according to claim 17, wherein said ratio ranges from 3:1 to 6:1.

19. The composition according to claim 1, wherein said amphiphilic lipid phase further comprises at least one ionic amphiphilic lipid.

20. The composition according to claim 19, wherein said at least one ionic amphiphilic lipid is chosen from anionic lipids, amphoteric lipids, and cationic lipids.

21. The composition according to claim 20, wherein said anionic amphiphilic lipids are chosen from alkaline salts of dicetyl and dimyristyl phosphate;

alkaline salts of cholesterol sulphate;

alkaline salts of cholesterol phosphate;

lipoamino acids;

sodium salts of phosphatidic acid;

phospholipids; and alkylsulphonic compounds.

22. The composition according to claim 21, wherein alkylsulphonic compounds are chosen from compounds of the following formula:

$$R-\underset{SO_3M}{CH}-CO-O-(CH_2-CH_2-CO)-CH_3$$

in which

R represents $C_{16}$–$C_{22}$ alkyl radicals, and M is an alkali metal.

23. The composition according to claim 20, wherein said cationic amphiphilic lipids are chosen from quaternary ammonium salts, fatty amines and salts thereof.

24. The composition according to claim 23, wherein said quaternary ammonium salts are chosen from:

compounds of formula (VIII):

$$\left[\begin{array}{c}R_1\\R_2\end{array}N\begin{array}{c}R_3\\R_4\end{array}\right]^+ X^-\quad\text{(VIII)}$$

in which the $R_1$ to $R_4$ radicals are independently chosen from linear and branched aliphatic radicals containing from 1 to 30 carbon atoms, and aromatic radicals and X is an anion chosen from halides, phosphates, acetates, lactates, ($C_2$–$C_6$)alkyl sulphates, and alkyl- and alkylarylsulphonates;

imidazolinium quaternary ammonium salts of formula (IX):

$$\left[\begin{array}{c}R_6\\ \phantom{x}\\ \end{array}\text{imidazoline ring with } CH_2-CH_2-N(R_8)-CO-R_5\right]^+ X^-\quad\text{(IX)}$$

in which $R_5$ is chosen from alkenyl and alkyl radicals containing from 8 to 30 carbon atoms, $R_6$ is chosen from a hydrogen atom, $C_1$–$C_4$ alkyl radicals and alkenyl and alkyl radicals containing from 8 to 30 carbon atoms, $R_7$ is chosen from $C_1$–$C_4$ alkyl radicals, $R_8$ is chosen from a hydrogen atom and $C_1$–$C_4$ alkyl radicals and X is an anion chosen from halides, phosphates, acetates, lactates, alkyl sulphates, and alkyl- and alkylarylsulphonates.

quaternary diammonium salts of formula (X):

$$\left[R_9-\underset{R_{11}}{\overset{R_{10}}{N}}-(CH_2)_3-\underset{R_{13}}{\overset{R_{12}}{N}}-R_{14}\right]^{++} 2X^-\quad\text{(X)}$$

in which $R_9$ is chosen from aliphatic radicals containing approximately from 16 to 30 carbon atoms, $R_{10}$, $R_{11}$, $R_{12}$, $R_{13}$ and $R_{14}$, which are identical or different, are chosen from a hydrogen atom and alkyl radicals containing from 1 to 4 carbon atoms and X is an anion chosen from halides, acetates, phosphates, nitrates and methyl sulphates, and quaternary ammonium salts containing at least one ester functional group.

25. The composition according to claim 24, wherein said aromatic radicals of formula (VIII) are chosen from aryls and alkylaryls and wherein said quaternary ammonium salts containing at least one ester functional group are chosen from compounds of formula (XI):

$$R_{17}-\overset{O}{\overset{\|}{C}}-(OC_nH_{2n})_y-\underset{R_{15}}{\overset{(C_rH_{2r}O)_z-R_{18}}{N^+}}-(C_pH_{2p}O)_x-R_{16}\quad X^-\quad\text{(XI)}$$

in which:

$R_{15}$ is chosen from $C_1$–$C_6$ alkyl radicals and $C_1$–$C_6$ hydroxyalkyl and dihydroxyalkyl radicals;

$R_{16}$ is chosen from:

$R_{19}$—C(O)— radicals saturated and unsaturated, linear and branched, $C_1$–$C_{22}$ hydrocarbon radicals $R_{20}$, and the hydrogen atom, $R_{18}$ is chosen from:

$R_{21}$—C(O)— radicals, saturated and unsaturated, linear and branched, $C_1$–$C_6$ hydrocarbon radicals $R_{22}$, and the hydrogen atom, $R_{17}$, $R_{19}$ and $R_{21}$ are independently chosen from saturated and unsaturated, linear and branched, $C_7$–$C_{21}$ hydrocarbon radicals;

n, p and r, which are identical or different, are integers having values from 2 to 6;

y is an integer having a value from 1 to 10;

x and z, which are identical or different, are integers having values from 0 to 10; and $X^-$ is an anion chosen from organic and inorganic, simple and complex anions;

with the proviso that the sum x+y+z has a value from 1 to 15, that when x has a value of 0, then $R_{16}$ denotes $R_{20}$, and that when z has a value of 0, then $R_{18}$ denotes $R_{22}$.

26. The composition according to claim 19, wherein said at least one ionic amphiphilic lipid is present in an amount ranging from 0 to 60% by weight with respect to the total weight of the amphiphilic lipid phase.

27. The composition according to claim 26, wherein said at least one ionic amphiphilic lipid is present in an amount ranging from 10 to 50%.

28. The composition according to claim 1, wherein the oil of said oil-in-water emulsion is present in an amount ranging from 5 to 40% by weight with respect to the total weight of the emulsion.

29. The composition according to claim 28, wherein the oil of said oil-in-water emulsion is present in an amount ranging from 10 to 30%.

30. The composition according to claim 17, wherein said oil is chosen from animal and vegetable oils formed by esters of fatty acids and of polyols;

natural and synthetic essential oils;

hydrocarbons;

halocarbons;

esters of an inorganic acid and of an alcohol;

ethers and polyethers; and silicones as a mixture with at least one of the oils defined above.

31. The composition according to claim 1, wherein said oil of said oil-in-water emulsion is present in an amount ranging from 0.1 to 15% by weight with respect to the total weight of the composition.

32. The composition according to claim 31, wherein said oil of said oil-in-water emulsion is present in an amount ranging from 0.2 to 10% by weight with respect to the total weight of the composition.

33. The composition according to claim 1, wherein said oil globules have a size ranging from 30 to 150 nm.

34. The composition according to claim 33, wherein said oil globules have a size ranging from 40 to 100 nm.

35. The composition according to claim 34, wherein said oil globules have a size ranging from 50 to 80 nm.

36. The composition according to claim 1, wherein said composition further comprises at least one ingredient chosen from water-soluble and fat-soluble active ingredients having cosmetic or dermopharmaceutical activity.

37. The composition according to claim 2, wherein said cosmetically appropriate medium comprises water or a mixture of water and at least one cosmetically acceptable solvent chosen from $C_1$–$C_4$ alcohol, alkylene glycols and glycol ethers.

38. The composition according to claim 1, wherein said composition has a final pH ranging from 3 to 10.

39. The composition according to claim 38, wherein said composition has a final pH ranging from 5 to 8.

40. The composition according to claim 1, wherein said composition further comprises viscosity regulating agents and thickeners.

41. The composition according to claim 1, wherein said composition has a further comprises up to 5% of pearlescent or opacifying agents.

42. The composition according to claim 1, wherein said composition further comprises at least one ingredient chosen from cationic surface-active agents, anionic, non-ionic, cationic and amphoteric polymers, proteins, protein hydrolysates, ceramides, pseudoceramides, fatty acids containing linear and branched $C_{16}$–$C_{40}$ chains, hydroxy acids, vitamins, panthenol, and volatile and non-volatile silicones.

43. The composition according to claim 1, wherein said composition is in the form of a thickened liquid, a cream or a gel.

44. A method of removing makeup from a keratinous substance comprising the step of applying to said keratinous substance a composition comprising:

(A) a washing base, wherein said washing base comprises at least one surfactant chosen from anionic surfactants chosen from the salts of alkyl sulphates, alkyl ether sulphates, alkylamido ether sulphates, alkylarylpolyether sulphates, monoglyceride sulphates, alkylsulphonates, alkyl phosphates, alkylamidesulphonates, alkylarylsulphonates, α-olefinsulphonates, paraffinsulphonates, alkyl sulphosuccinates, alkyl ether sulphosuccinates, alkylamidesulphosuccinates, alkyl sulphosuccinamates, alkyl sulphoacetates, alkyl ether phosphates, acylsarcosinates, acylisethionates and N-acyltaurates;

alkyl-D-galactosideuronic acids, polyoxyalkylenated ($C_6$–$C_{24}$)alkyl ether carboxylic acids, polyoxyalkylenated ($C_6$–$C_{24}$)alkylaryl ether carboxylic acids, polyoxyalkylenated ($C_6$–$C_{24}$)alkylamido ether carboxylic acids and salts thereof;

the salts of fatty acids chosen from oleic, ricinoleic, palmitic and stearic acids, the acids of copra oil, the acids of hydrogenated copra oil, and the salts of acyllactylates in which the acyl radical contains 8 to 20 carbon atoms;

nonionic surfactants chosen from polyethoxylated, polypropoxylated and polyglycerolated fatty alcohols, alphadiols, alkylphenols and acids, having a fatty chain;

copolymers of ethylene and propylene oxide and the condensates of ethylene and propylene oxide with fatty alcohols;

polyethoxylated fatty amides, polyglycerolated fatty amides, oxyethylenated esters of sorbitan fatty acids, sucrose esters of fatty acids, alkylpolyglycosides, polyethylene glycol esters of fatty acids, N-alkylglucamine derivatives, and amine oxides;

amphoteric surfactants chosen from derivatives of aliphatic secondary or tertiary amines containing at least one water-solubizing anionic group and further wherein said aliphatic radical contains 8 to 22 carbon atoms; ($C_8$–$C_{20}$)alkylbetaines, sulphobetaines, ($C_8$–$C_{20}$)alkylamido($C_1$–$C_6$)alkylbetaines, and ($C_8$–$C_{20}$)alkylamido($C_1$–$C_6$)alkylsulphobetaines; and cationic surfactants chosen from the salts of optionally polyoxyalkylenated primary, secondary and tertiary fatty amines, quaternary ammonium salts, imidazoline derivatives, and amine oxides of cationic nature;

and (B) a conditioning system comprising at least one oil-in-water emulsion having oil globules with a mean size of less than 150 nm and comprising an amphiphilic lipid phase, said amphiphilic lipid phase comprising at least one non-ionic amphiphilic lipid which is liquid at a temperature of less than 45° C., wherein said composition is applied in an amount effective for removing make-up from said keratinous substance.

45. A method of cleaning a keratinous substance comprising the step of applying to said keratinous substance a composition comprising:

(A) a washing base, wherein said washing base comprises at least one surfactant chosen from anionic surfactants chosen from the salts of alkyl sulphates, alkyl ether sulphates, alkylamido ether sulphates, alkylarylpolyether sulphates, monoglyceride sulphates, alkylsulphonates, alkyl phosphates, alkylamidesulphonates, alkylarylsulphonates, α-olefinsulphonates, paraffinsulphonates, alkyl sulphosuccinates, alkyl ether sulphosuccinates, alkylamidesulphosuccinates, alkyl sulphosuccinamates, alkyl sulphoacetates, alkyl ether phosphates, acylsarcosinates, acylisethionates and N-acyltaurates;

alkyl-D-galactosideuronic acids, polyoxyalkylenated $(C_6-C_{24})$alkyl ether carboxylic acids, polyoxyalkylenated $(C_6-C_{24})$alkylaryl ether carboxylic acids, polyoxyalkylenated $(C_6-C_{24})$alkylamido ether carboxylic acids and salts thereof;

the salts of fatty acids chosen from oleic, ricinoleic, palmitic and stearic acids, the acids of copra oil, the acids of hydrogenated copra oil, and the salts of acyl-lactylates in which the acyl radical contains 8 to 20 carbon atoms;

nonionic surfactants chosen from polyethoxylated, polypropoxylated and polyglycerolated fatty alcohols, alphadiols, alkylphenols and acids, having a fatty chain;

copolymers of ethylene and propylene oxide and the condensates of ethylene and propylene oxide with fatty alcohols;

polyethoxylated fatty amides, polyglycerolated fatty amides, oxyethylenated esters of sorbitan fatty acids, sucrose esters of fatty acids, alkylpolyglycosides, polyethylene glycol esters of fatty acids, N-alkylglucamine derivatives, and amine oxides;

amphoteric surfactants chosen from derivatives of aliphatic secondary or tertiary amines containing at least one water-solubizing anionic group and further wherein said aliphatic radical contains 8 to 22 carbon atoms; $(C_8-C_{20})$alkylbetaines, sulphobetaines, $(C_8-C_{20})$alkylamido$(C_1-C_6)$alkylbetaines, and $(C_8-C_{20})$alkylamido$(C_1-C_6)$alkylsulphobetaines; and cationic surfactants chosen from the salts of optionally polyoxyalkylenated primary, secondary and tertiary fatty amines, quaternary ammonium salts, imidazoline derivatives, and amine oxides of cationic nature;

and (B) a conditioning system comprising at least one oil-in-water emulsion having oil globules with a mean size of less than 150 nm and comprising an amphiphilic lipid phase, said amphiphilic lipid phase comprising at least one non-ionic amphiphilic lipid which is liquid at a temperature of less than 45° C., wherein said composition is applied in an amount effective for removing make-up from said keratinous substance.

46. A method of conditioning a keratinous substance comprising the step of applying to said keratinous substance a composition comprising:

(A) a washing base, wherein said washing base comprises at least one surfactant chosen from anionic surfactants chosen from the salts of alkyl sulphates, alkyl ether sulphates, alkylamido ether sulphates, alkylarylpolyether sulphates, monoglyceride sulphates, alkylsulphonates, alkyl phosphates, alkylamidesulphonates, alkylarylsulphonates, α-olefinsulphonates, paraffinsulphonates, alkyl sulphosuccinates, alkyl ether sulphosuccinates, alkylamidesulphosuccinates, alkyl sulphosuccinamates, alkyl sulphoacetates, alkyl ether phosphates, acylsarcosinates, acylisethionates and N-acyltaurates;

alkyl-D-galactosideuronic acids, polyoxyalkylenated $(C_6-C_{24})$alkyl ether carboxylic acids, polyoxyalkylenated $(C_6-C_{24})$alkylaryl ether carboxylic acids, polyoxyalkylenated $(C_6-C_{24})$alkylamido ether carboxylic acids and salts thereof;

the salts of fatty acids chosen from oleic, ricinoleic, palmitic and stearic acids, the acids of copra oil, the acids of hydrogenated copra oil, and the salts of acyl-lactylates in which the acyl radical contains 8 to 20 carbon atoms;

nonionic surfactants chosen from polyethoxylated, polypropoxylated and polyglycerolated fatty alcohols, alphadiols, alkylphenols and acids, having a fatty chain;

copolymers of ethylene and propylene oxide and the condensates of ethylene and propylene oxide with fatty alcohols;

polyethoxylated fatty amides, polyglycerolated fatty amides, oxyethylenated esters of sorbitan fatty acids, sucrose esters of fatty acids, alkylpolyglycosides, polyethylene glycol esters of fatty acids, N-alkylglucamine derivatives, and amine oxides;

amphoteric surfactants chosen from derivatives of aliphatic secondary or tertiary amines containing at least one water-solubizing anionic group and further wherein said aliphatic radical contains 8 to 22 carbon atoms; $(C_8-C_{20})$alkylbetaines, sulphobetaines, $(C_8-C_{20})$alkylamido$(C_1-C_6)$alkylbetaines, and $(C_8-C_{20})$alkylamido$(C_1-C_6)$alkylsulphobetaines; and cationic surfactants chosen from the salts of optionally polyoxyalkylenated primary, secondary and tertiary fatty amines, quaternary ammonium salts, imidazoline derivatives, and amine oxides of cationic nature;

and (B) a conditioning system comprising at least one oil-in-water emulsion having oil globules with a mean size of less than 150 nm and comprising an amphiphilic lipid phase, said amphiphilic lipid phase comprising at least one non-ionic amphiphilic lipid which is liquid at a temperature of less than 45° C., wherein said composition is applied in an amount effective for removing make-up from said keratinous substance.

47. A method of washing and/or conditioning a keratinous substance comprising the steps of:

applying to wet said keratinous substance a composition comprising:

(A) a washing base, wherein said washing base comprises at least one surfactant chosen from anionic surfactants chosen from the salts of alkyl sulphates, alkyl ether sulphates, alkylamido ether sulphates, alkylarylpolyether sulphates, monoglyceride sulphates, alkylsulphonates, alkyl phosphates, alkylamidesulphonates, alkylarylsulphonates, α-olefinsulphonates, paraffinsulphonates, alkyl sulphosuccinates, alkyl ether sulphosuccinates, alkylamidesulphosuccinates, alkyl sulphosuccinamates, alkyl sulphoacetates, alkyl ether phosphates, acylsarcosinates, acylisethionates and N-acyltaurates;

alkyl-D-galactosideuronic acids, polyoxyalkylenated $(C_6-C_{24})$alkyl ether carboxylic acids, polyoxyalkylenated $(C_6-C_{24})$alkylaryl ether carboxylic acids, polyoxyalkylenated $(C_6-C_{24})$alkylamido ether carboxylic acids and salts thereof;

the salts of fatty acids chosen from oleic, ricinoleic, palmitic and stearic acids, the acids of copra oil, the acids of hydrogenated copra oil, and the salts of acyllactylates in which the acyl radical contains 8 to 20 carbon atoms;

nonionic surfactants chosen from polyethoxylated, polypropoxylated and polyglycerolated fatty alcohols, alphadiols, alkylphenols and acids, having a fatty chain;

copolymers of ethylene and propylene oxide and the condensates of ethylene and propylene oxide with fatty alcohols;

polyethoxylated fatty amides, polyglycerolated fatty amides, oxyethylenated esters of sorbitan fatty acids, sucrose esters of fatty acids, alkylpolyglycosides, polyethylene glycol esters of fatty acids, N-alkylglucamine derivatives, and amine oxides;

amphoteric surfactants chosen from derivatives of aliphatic secondary or tertiary amines containing at least one water-solubizing anionic group and further wherein said aliphatic radical contains 8 to 22 carbon atoms; $(C_8-C_{20})$alkylbetaines, sulphobetaines, $(C_8-C_{20})$alkylamido$(C_1-C_6)$alkylbetaines, and $(C_8-C_{20})$alkylamido$(C_1-C_6)$alkylsulphobetaines; and cationic surfactants chosen from the salts of optionally polyoxyalkylenated primary, secondary and tertiary fatty amines, quaternary ammonium salts, imidazoline derivatives, and amine oxides of cationic nature;

and (B) a conditioning system comprising at least one oil-in-water emulsion having oil globules with a mean size of less than 150 nm and comprising an amphiphilic lipid phase, said amphiphilic lipid phase comprising at least one non-ionic amphiphilic lipid which is liquid at a temperature of less than 45° C., wherein said composition is applied in an amount effective for removing make-up from said keratinous substance, generating foam by massaging or rubbing with the hands, and rinsing with water after an optional period of rest.

\* \* \* \* \*

UNITED STATES PATENT AND TRADEMARK OFFICE
CERTIFICATE OF CORRECTION

PATENT NO. : 6,488,780 B2
DATED : December 3, 2002
INVENTOR(S) : Daniéle Cauwet-Martin It is certified that error appears in the above-identified patent and that said Letters Patent is hereby corrected as shown below:

<u>Title page,</u>
Item [75], in the named Inventor, "Daniéle" should read -- Danièle --.

<u>Column 14,</u>
Line 53, "water-solubizing" should read -- water-solubilizing --.

<u>Column 15,</u>
Line 60, "$R_2$-CONHCH$_2$CH$_2$-N(B)(C)" should read -- $R_{2'}$-CONHCH$_2$CH$_2$-N(B)(C) --.

<u>Column 16,</u>
Line 3, "$R_{2'}$denotes and" should read -- $R_{2'}$ denotes an --.
Line 62, "HO-(OCH$_2$CH$_2$)$_y$-(CH$_2$)$_3$[(CH$_3$)$_2$SiO]$_{A'}$-(CH$_2$)$_3$-" should read
-- HO-(OCH$_2$CH$_2$)$_y$-(CH$_2$)$_3$-[(CH$_3$)$_2$SiO]$_{A'}$-(CH$_2$)$_3$- --.

<u>Column 17,</u>
Line 34, before "alkylsulphonic", insert -- said --.

<u>Column 20,</u>
Line 7, after "composition", delete "has a".
Line 60, "water-solubizing" should read -- water-solubilizing --.

<u>Column 21,</u>
Line 54, "water-solubizing" should read -- water-solubilizing --.

<u>Column 22,</u>
Line 48, "water-solubizing" should read -- water-solubilizing --.

UNITED STATES PATENT AND TRADEMARK OFFICE
CERTIFICATE OF CORRECTION

PATENT NO. : 6,488,780 B2
DATED : December 3, 2002
INVENTOR(S) : Daniéle Cauwet-Martin It is certified that error appears in the above-identified patent and that said Letters Patent is hereby corrected as shown below:

Column 24,
Line 9, "water-solubizing" should read -- water-solubilizing --.

Signed and Sealed this

Fifteenth Day of April, 2003

JAMES E. ROGAN
*Director of the United States Patent and Trademark Office*